United States Patent [19]

Mabe et al.

[11] Patent Number: 4,698,307
[45] Date of Patent: Oct. 6, 1987

[54] RECOMBINANT DNA CLONING VECTORS CONTAINING SELECTABLE GENETIC MARKERS FOR USE IN STREPTOMYCES AND RELATED ORGANISMS

[75] Inventors: James A. Mabe; Walter M. Nakatsukasa, both of Indianapolis, Ind.

[73] Assignee: Eli Lilly and Company, Indianapolis, Ind.

[21] Appl. No.: 639,631

[22] Filed: Aug. 10, 1984

[51] Int. Cl.[4] ................ C12N 1/20; C12N 15/00; C12P 21/00; C12P 19/34; C12N 1/00; C12R 1/465; C12R 1/485; C12R 1/54; C07H 21/04

[52] U.S. Cl. ................ 435/253; 435/68; 435/91; 435/172.3; 435/243; 435/317; 435/886; 435/889; 435/896; 536/27; 935/6; 935/29; 935/75; 935/320

[58] Field of Search .......... 435/68, 70, 91, 172.3, 435/253, 317, 886, 889, 896, 243; 536/27; 935/6, 29, 75

[56] References Cited

U.S. PATENT DOCUMENTS 4,416,994 11/1983 Nakatsukasa et al. ............. 435/253

FOREIGN PATENT DOCUMENTS 7901169 12/1979 PCT Int'l Appl. .

OTHER PUBLICATIONS

Rodgers et al, "Cloning and Expression of a Streptomyces fradie Neomycin Resistance Gene in Escherichia coli" Gene 18: 133 (1982).

Thompson et al, "Physical Analysis of Antibiotic-Resistance Genes from Streptomyces and Their Use in Vector Construction", Gene 20: 51 (1982).

Schupp et al, "Expression of a Neomycin Phosphotransferase Gene from Streptomyces fradiae in Escherichia coli after Interplasmidic Recombination", Mol Gen. Genet. (189: 27 (1983).

Thompson, C. et al., 1980, Nature 286:525.

Hopwood, D. A. et al., 1983, Trends in Biotechnology, 1:42.

Katz, E. et al., 1983, J. Gen. Microbiol. 129:2703.

Richardson, M. et al., 1982, Gene 20:451.

Primary Examiner—James Martinell
Attorney, Agent, or Firm—Ron K. Levy; Leroy Whitaker

[57] ABSTRACT

The present invention disclosed novel recombinant DNA cloning vectors including pMND1000 and vectors derived therefrom for use in Streptomyces and related organisms. These novel cloning vectors contain genetic markers that provide antibiotic resistance or colorimetric selectivity to the host cells. The invention further comprises transformants of the aforementioned vectors.

24 Claims, 7 Drawing Figures

Restriction Site Map of Plasmid pMND1000 pMND 1000

Restriction Site Map of Plasmid pMND1000

Restriction Map of ~1.5 kb
BclI Tyrosinase Gene Fragment

Figure 3
Restriction Site and Functional Map of Plasmids pMND1001 and pMND1001A
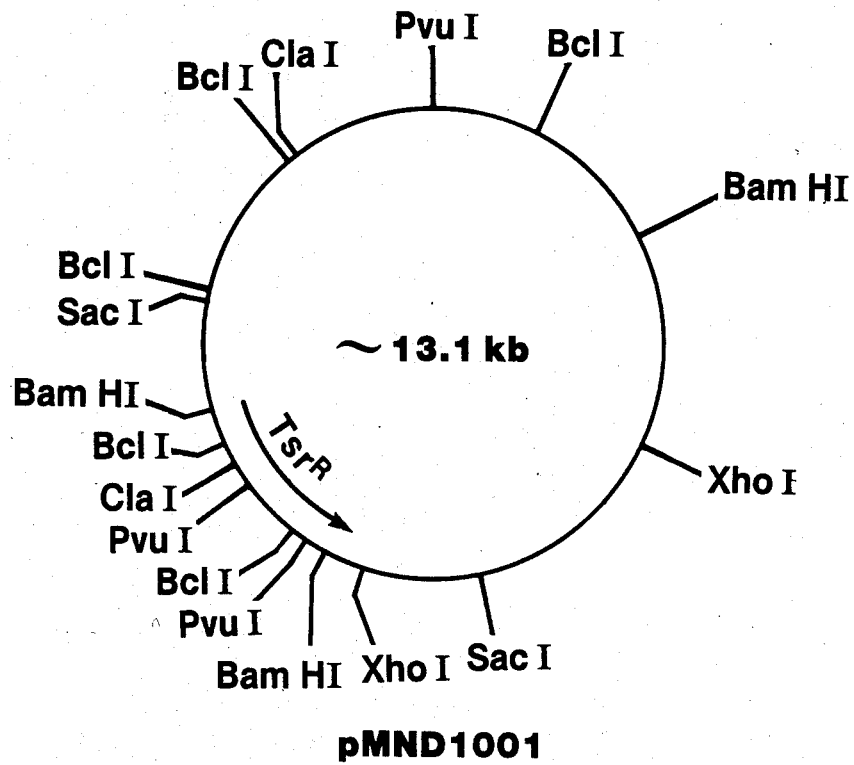
pMND1001
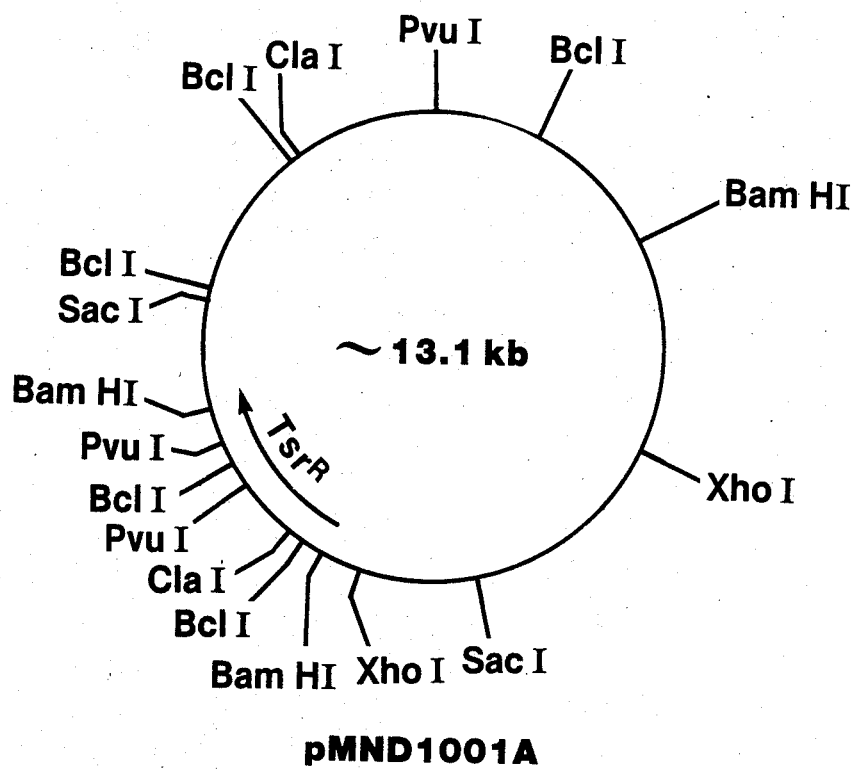
pMND1001A

Figure 5
Restriction Site and Functional Map of Plasmids pMND1004A and pMND1004B
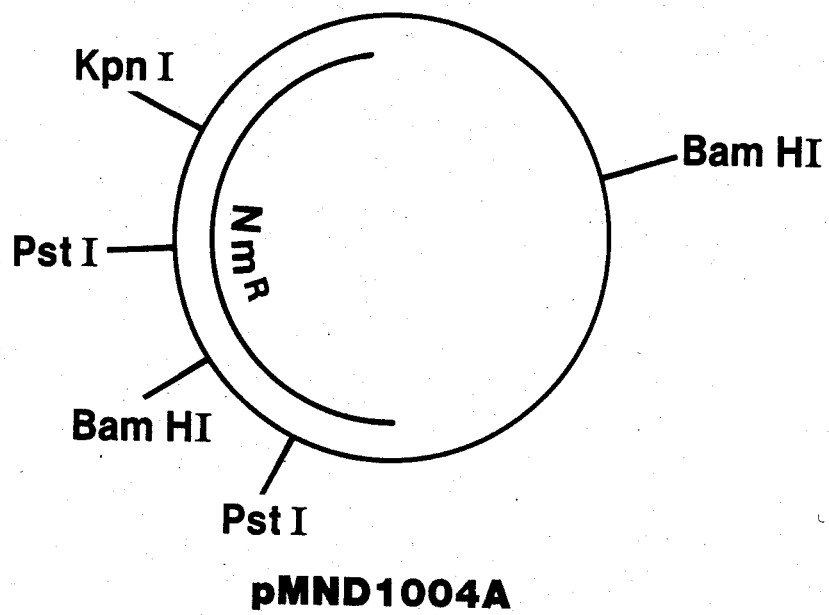
pMND1004A
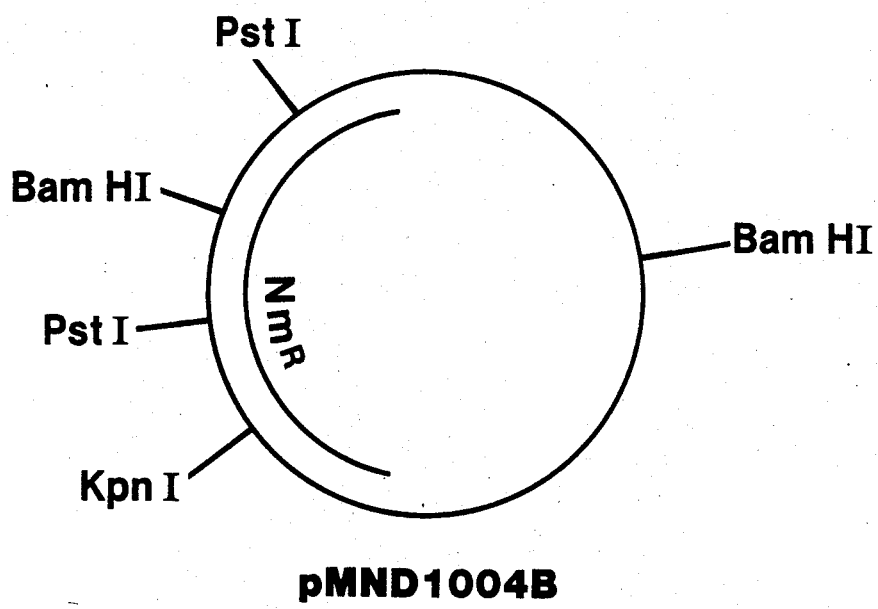
pMND1004B

Figure 6
Restriction Site and Functional Map of Plasmids pMND1005A and pMND1005B
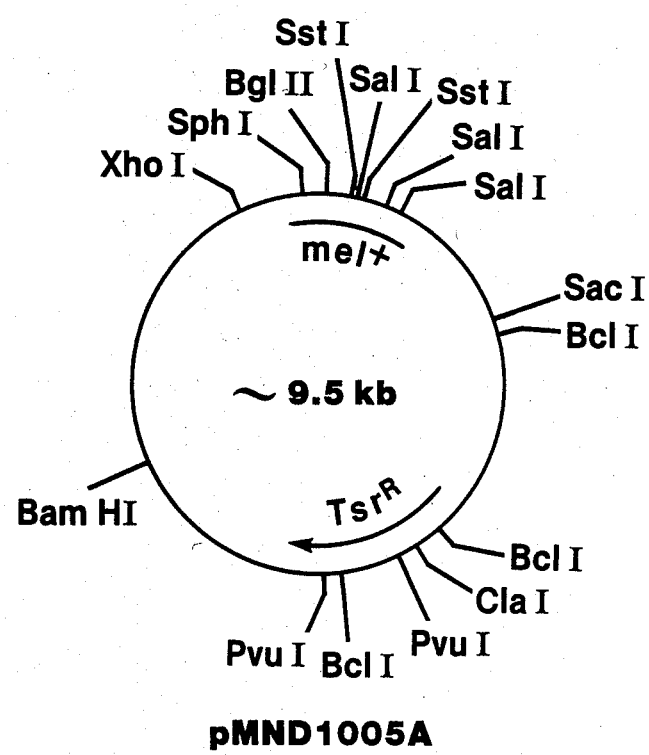
pMND1005A
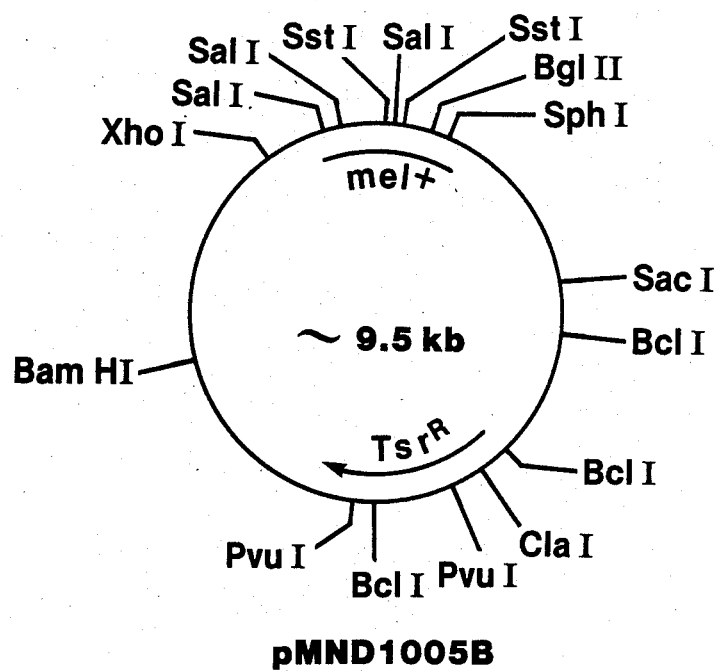
pMND1005B

Figure 7
Restriction Site and Functional Map
of Plasmids pMND1006A and pMND1006B
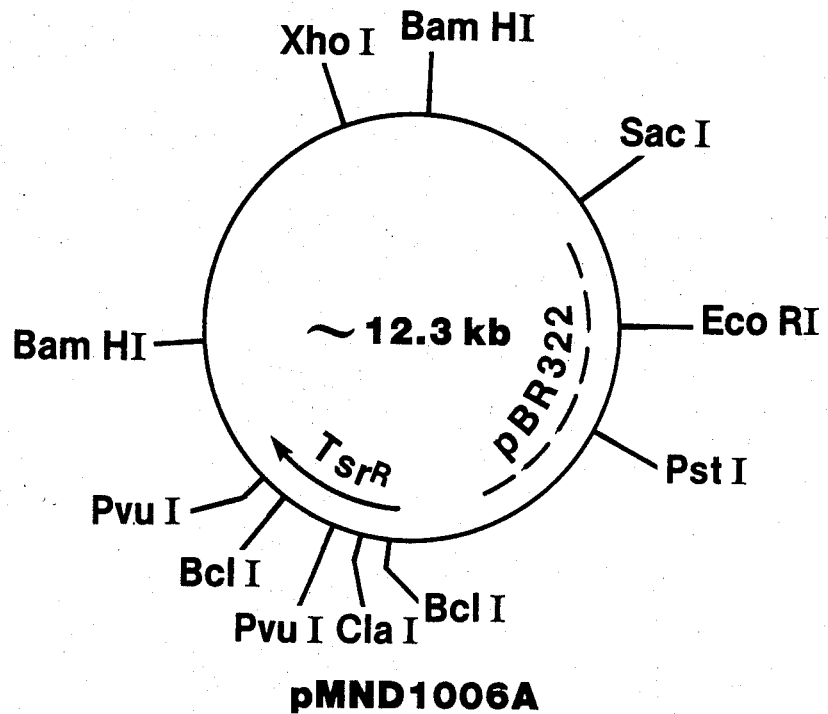
pMND1006A
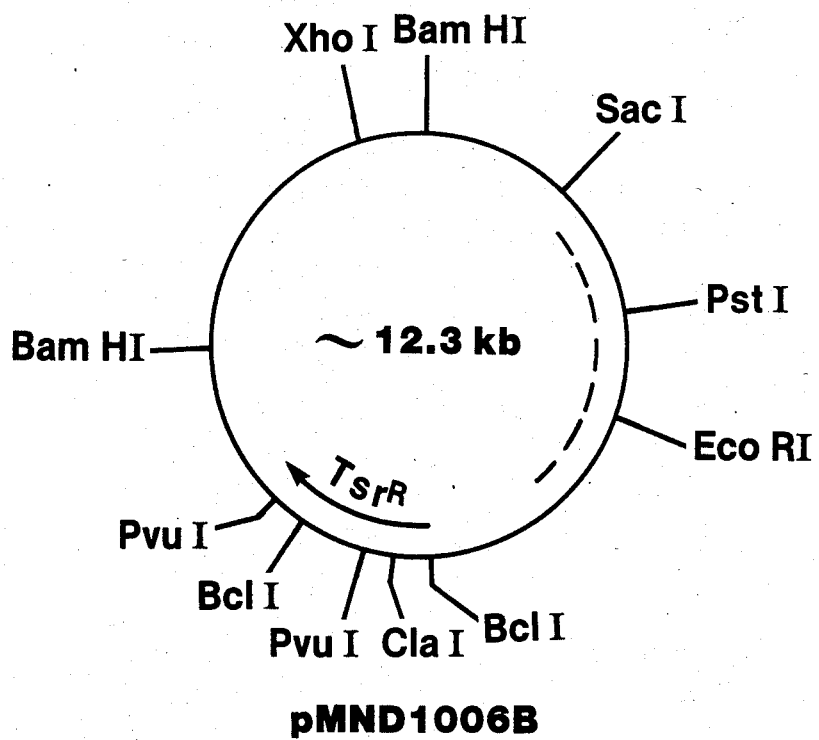
pMND1006B

RECOMBINANT DNA CLONING VECTORS CONTAINING SELECTABLE GENETIC MARKERS FOR USE IN STREPTOMYCES AND RELATED ORGANISMS

SUMMARY OF THE INVENTION

The present invention comprises novel recombinant DNA cloning vectors comprising a functional origin of replication-containing restriction fragment of plasmid pMND1000 and one or more DNA segments that provide selectable genetic markers. The invention further comprises transformants of the aforementioned vectors.

The present invention provides antibiotic resistance conferring or colorimetric selectable cloning vectors for use in Streptomyces and related host cells. Heretofore, the development and exploitation of recombinant DNA technology in the above organisms has been retarded and made especially difficult because of the general lack of selectable genetic markers on cloning vectors. The vectors of the present invention are functional and selectable in both Streptomyces and other host strains and therefore represent a significant advance in the technical art.

The present vectors are particularly useful because they are relatively small, versatile, and can transform and be selected in any Streptomyces cell that is sensitive to an antibiotic for which resistance is conveyed or is capable of expressing a colorimetric phenotype. Since more than seventy percent of naturally occurring antibiotics are produced by Streptomyces strains, it is desirable to develop cloning systems and vectors that are applicable to that industrially important group. The present invention provides such vectors and thus allows for the cloning of genes into Streptomyces both for increasing the yields of known antibiotics as well as for the production of new antibiotics and antibiotic derivatives.

The present invention provides vehicles for cloning DNA into Streptomyces host cells and also allows for the convenient selection of transformants. Since transformation is a very low frequency event, such a functional test is a practical necessity for determining which cell(s), of among the billions of cells, has acquired the plasmid DNA. This is important because DNA sequences that are themselves non-selectable can be inserted into the vectors and, upon transformation, cells containing the vector and the particular DNA sequence of interest can be isolated either by appropriate antibiotic selection or colorimetric assay analysis.

For purposes of the present invention as disclosed and claimed herein, the following terms are as defined below.

Recombinant DNA Cloning Vector—any autonomously replicating agent, including but not limited to plasmids, comprising a DNA molecule to which one or more additional DNA segments can or have been added.

Transformation—the introduction of DNA into a recipient host cell that changes the genotype and consequently results in a change in the recipient cell.

Transformant—a recipient host cell that has undergone transformation.

Sensitive Host Cell—a host cell that cannot grow in the presence of a given antibiotic without a DNA segment that confers resistance thereto or a host cell capable of expressing a gene conferring a colorimetric phenotype.

Restriction Fragment—any linear DNA generated by the action of one or more restriction enzymes.

Insertional Isomer—one of the two or more possible recombinant DNA molecules formed when a DNA fragment is inserted at one of two or more compatible sites on the recipient DNA.

E. coli Origin of Replication—a DNA sequence that controls and allows for replication and maintenance of plasmid or other vector in E. coli.

Streptomyces Origin of Replication—a DNA sequence that controls and allows for replication and maintenance of plasmid or other vector in Streptomyces.

Genetic Marker—a gene or combination of genes of known function and location on a chromosome or recombinant DNA cloning vector.

$Ap^R$—the ampicillin resistant phenotype.
$Tet^S$—the tetracycline sensitive phenotype.
$Tsr^R$—the thiostrepton resistant phenotype.
$Nm^R$—the neomycin resistant phenotype.
mel+—the melanin producing phenotype.

DETAILED DESCRIPTION OF THE INVENTION

The present invention comprises recombinant DNA cloning vectors comprising:
(a) a functional origin of replication-containing restriction fragment of plasmid pMND1000, and
(b) one or more DNA segments that convey resistance to at least one antibiotic or that convey colorimetric selectivity when transformed into a sensitive restrictionless host cell.

The invention further comprises transformants of the aforementioned vectors.

The vectors of the present invention are constructed by ligating one or more antibiotic resistance-conferring DNA segments or colorimetric gene-containing DNA fragments to an origin of replication-containing restriction fragment of plasmid pMND1000. Plasmid pMND1000, from which the origin of replication-containing restriction fragments are obtained, is approximately 11.5 kb and contains several restriction sites which are particularly advantageous for molecular cloning. Since the origin of replication and maintenance region of plasmid pMND1000 has been localized to within the ~3.4 kb XhoI-BclI restriction fragment, a variety of different origin of replication containing fragments can be generated by digesting the plasmid with restriction enzymes that cut outside or possibly, inside the ~3.4 kb XhoI-BclI region, as long as the origin of replication is not disrupted. A detailed restriction site map of plasmid pMND1000 is presented in FIG. 1 of the accompanying drawings. The restriction endonuclease abbreviations shown in the drawings are standard and well-known in the art. For purposes of the present application, FIG. 1 and all subsequent figures are not drawn to scale.

Plasmid pMND1000 can be conventionally isolated from Streptomyces lividans, a constructed strain deposited and made part of the permanent stock culture collection of the Northern Regional Research Laboratory, Peoria, Ill. 61604. The strain is available to the public, as a preferred source and stock reservoir of the plasmid, under the accession number NRRL 15808. Streptomyces lividans carries two different plasmids that can be conventionally isolated and separated on the basis of size and the pattern of restriction sites.

Although many different origin of replication-containing fragments of plasmid pMND1000 can be constructed, the fragment exemplified herein for illustrative purposes is the ~3.4 kb XhoI-BclI restriction fragment. This fragment can be independently ligated to one or more antibiotic resistance-conferring DNA fragments or colorimetric gene-containing DNA fragments, exemplified herein for illustrative purposes by the thiostrepton resistance-containing ~1.6 kb BamHI restriction fragment of plasmid pLR2, the neomycin resistance-conferring ~3.4 kb BamHI restriction fragment of plasmid, pLR1, and the ~1.5 kb BclI tyrosinase gene-containing fragment of plasmid pIJ702, to form vectors illustrative of the present invention.

Plasmids pLR2 and pLR1, respective sources of the thiostrepton and neomycin resistance-conferring fragments, are constructed in accordance with and are the subject of U.S. Pat. No. 4,416,994. *Streptomyces lividans*/pIJ702 (ATCC 39155) is the source of the tyrosinase gene-containing DNA fragment which is responsible for melanin synthesis and produces a mel+ phenotype in its host organism. The expression of a mel+ phenotype is both strain and media dependent. For example, when *Streptomyces lividans* colonies are plated on tryptic soy agar (available from Difco Laboratories, P.O. Box 1058A, Detroit, Mich. 48232), the mel+ phenotype is expressed as a black pigment releasing colony. Thus, this assay provide for the convenient selection of transformants. A restriction map of the tyrosinase gene is presented in FIG. 2 of the accompanying drawings.

For convenience and ease of construction the thiostrepton resistance-conferring ~1.6 kb BamHI fragment, the neomycin resistance-conferring ~3.4 kb BamHI fragment, and the ~1.5 kb BclI tyrosinase gene-containing fragment are ligated to the ~3.4 kb XhoI-BclI origin of replication-containing fragment of plasmid pMND1000. The resulting recombinant DNA is then ligated to produce plasmids illustrative of the present invention. Thus, ligation of the ~3.4 kb BamHI fragment of plasmid pLR1 to the ~3.4 kb XhoI-BclI fragment of plasmid pMND1000 results in illustrative plasmids pMND1004A and pMND1004B. Similarly, ligation of the ~1.6 kb BamHI frgment of plasmid pLR2 to BclI-deleted plasmid pMND1000 results in illustrative plasmids pMND1002 and pMND1002A. Additionally, ligation of the ~1.5 kb BclI of plasmid pIJ702 to XhoI-deleted plasmid pMND1002 results in illustrative plasmids pMND1005A and pMND1005B.

The ligations used to construct illustrative plasmids pMND1003 and pMND1003A are made possible by the fact that some restriction enzymes, such as BclI and BamHI, generate compatible cohesive ends. However, in a few cases, fragments generated by one restriction enzyme when ligated to fragments generated by a second enzyme give rise to recombinants that are recognized by neither of the parental enzymes. For example, when fragments generated by BclI (T ↓ GATCA) are ligated to fragments generated by BamHI (G ↓ GATCC), the resulting recombinant target sites are cleaved by neither BclI nor BamHI.

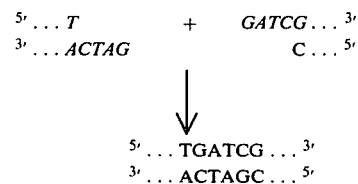

Similarly, recombinant plasmids can be constructed by ligating BclI-restricted fragments to BamHI-restricted fragments to generate illustrative plasmids pMND1002, pMND1002A, pMND1004A and pMND1005B.

Various plasmid pMND1000 restriction fragments can be used for the ligation to antibiotic resistance-conferring DNA segments provided that the origin of replication contained in the ~3.4 kb XhoI-BclI restriction fragment is present. Additional plasmid pMND1000 restriction fragments, useful for constructing illustrative plasmids within the scope of the present invention, include, but are not limited to, the ~6.1 kb BclI-XhoI or ~9 kb BclI fragment. A particular antibiotic resistance-conferring DNA segment or colorimetric gene-containing DNA segment is not limited to a single position on a plasmid pMND1000 fragment but can be ligated or inserted into varying sites provided that the origin of replication or other necessary plasmid contained physiological functions are not disrupted. Those skilled in the art understand or can readily determine which sites are advantageous for the ligation or insertion of a particular DNA segment.

Although the thiostrepton and neomycin antibiotic resistance-conferring DNA segments exemplified herein are respectively the ~1.6 kb BamHI and ~3.4 kb BamHI restriction fragments of plasmids pLR2 and pLR1, those skilled in the art can construct and use, either individually or in combination, additional DNA segments that also confer resistance to thiostrepton and neomycin. Additional thiostrepton resistance-conferring DNA segments of plasmid pLR2 include, for example, the ~1 kb BclI restriction fragment. Additional neomycin resistance-conferring DNA segments of plasmid pLR1 include, for example, the ~3.5 kb PstI restriction fragment and also the larger of the SacI-KpnI fragments of the ~3.4 kb BamHI restriction fragment.

Still other DNA segments that confer resistance to the same or to different antibiotics such as, for example, chloramphenicol, streptomycin, hygromycin, puromycin, viomycin, tylosin, erythromycin, vancomycin, actaplanin, and the like can also be constructed and used by those skilled in the art.

Functional derivatives of the various antibiotic resistance-conferring DNA segments or colorimetric gene-containing DNA segments can be made by adding, eliminating, or substituting certain nucleotides in accordance with the genetic code. Those skilled in the art will understand that ligation of these modified segments, or any other antibiotic resistance-conferring DNA segment or colorimetric gene-containing DNA segment, to an origin of replication-containing fragment of plasmid pMND1000 results in vectors that are also within the scope of the present invention.

Derivative vectors that further exemplify the invention can also be constructed. For example, XhoI deletion of plasmid pMND1002 results in illustrative plasmid pMND1003, a plasmid from which additional derivatives can also be made. Thus, insertion of the plasmid pIJ702 ~1.5 kb BclI tyrosinase gene-containing fragment into plasmid pMND1003 results in illustrative plasmids pMND1005A and pMND1005B. The aforementioned antibiotic resistance-conferring and colorimetric gene-containing derivative plasmids contain the plasmid pMND1000 origin of replication and are therefore within the scope of the present invention.

The present Streptomyces-functional vectors such as, for example, plasmids pMND1001, pMND1001A, pMND1002, pMND1002A, pMND1003, MND1004A, pMND1004B, pMND1005A and pMND1005B can be ligated to a functional replicon-containing and antibiotic resistance-conferring restriction fragment of a variety of E. coli plasmids such as, for example, plasmids pBR322, pBR325, pBR328 and the like, to produce self-replicating bifunctional vectors that are selectable in both E. coli and Streptomyces.

These bifunctional constructions comprise the pMND1000 Streptomyces origin of replication, a DNA segment that confers antibiotic resistance or colorimetric gene-selectivity in Streptomyces, a replicon that is functional in E. coli and also a DNA segment that confers antibiotic resistance in E. coli. Bifunctional constructions, exemplified herein by plasmids pMND1006A and pMND1006B, are particularly advantageous because amplification and manipulation of plasmids can be done faster and more conveniently in E. coli than in Streptomyces. Thus, after desired recombinant DNA procedures are accomplished within the E. coli host system, the entire plasmid or particular Streptomyces DNA can be removed, and re-constructed (if necessary) to plasmid form, and then transformed into a Streptomyces or related host cell.

The recombinant DNA cloning vectors of the present invention are not limited for use in a single species or strain of Streptomyces. To the contrary, the vectors are broadly applicable and can be transformed into host cells of many Streptomyces taxa, particularly restrictionless strains of economically important taxa that produce antibiotics such as aminoglycoside, macrolide, β-lactam, polyether, and glycopeptide antibiotics and the like. Such restrictionless strains are readily selected and isolated from Streptomyces taxa by conventional procedures well known in the art (Lomovskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

Preferred host cells of restrictionless strains of Streptomyces taxa that produce aminoglycoside antibiotics and in which the present vectors are especially useful and can be transformed, include restrictionless cells of, for example: *Streptomyces kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. tenebrarius* (tobramycin, apramycin), *S. lavendulae* (neomycin), *S. albogriseolus* (neomycins), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. fradiae* (hybrimycins neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex), and *S. canus* (ribosyl paromamine).

Preferred host cells of restrictionless strains of Streptomyces taxa that produce macrolide antibiotics and in which the present vectors are especially useful and can be transformed, include restrictionless cells of, for example: *Streptomyces caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (agromycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetyl-leukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. alborgriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), and *S. albireticuli* (carbomycin).

Preferred host cells of restrictionless strains of Streptomyces taxa that produce β-lactam antibiotics and in which the present vectors are especially useful and can be transformed, include restrictionless cells of, for example: *Streptomyces lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogenes* (cephamycins A, B); *S. cattleya* (thienamycin); and *S. olivaceus, S. flavovirens, S. flavus, S. fulvoviridis, S. argenteolus,* and *S. sioyaensis* (MM 4450 and MM 13902).

Preferred host cells of restrictionless strains of Streptomyces taxa that produce polyether antibiotics and in which the present vectors are especially usefull and can be transformed, include restrictionless cells of, for example: *Streptomyces albus* (A204, A28695A and B, salinomycin), *S. hygroscopicus* (A218, emericid, DE3936), A120A, A28695A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

Preferred host cells of restrictionless strains of Streptomyces taxa that produce glycopeptide antibiotics in which the present vectors are especially useful and can be transformed, include restrictionless cells of, for example: *Streptomyces orientalis* and *S. haranomachiensis* (vancomycin); *S. candidus* (A-35512, avoparcin), *S. eburosporeus* (LL-AM 374), and *S. toyocaensis* (A47934).

Preferred host cells of other *Streptomyces* restrictionless strains in which the present vectors are especially useful and can be transformed, include restrictionless cells of, for example: *Streptomyces coelicolor, S. granuloruber, S. roseoporus, S. lividans, S. tenebrarius, S. acrimycins, S. glaucescens, S. parvilin, S. pristinaespiralis, S. violaceoruber, S. vinaceus, S. virginiae, S. espinosus,* and *S. azureus.*

In addition to the representative *Streptomyces* host cells described above, the present vectors are also useful and can be transformed into cells of restrictionless strains of other taxa such as, for example: *Bacillus, Staphylococcus* and related Actinomycetes, including *Streptosporangium, Actinoplanes, Nocardia,* and *Micromonospora.* Thus, the vectors of the present invention have wide application and are useful and can be transformed into host cells of a variety of organisms.

While all the embodiments of the present invention are useful, some of the present recombinant DNA cloning vectors and transformants are preferred. Accordingly, preferred vectors are plasmids pMND1001, pMND1002, pMND1003, pMND1004A, and pMND1006A; and preferred transformants are *Streptomyces lividans*/pMND1001, *S. lividans*/pMND1002 *S. lividans*/pMND1003, *S. lividans*/pMND1004A, *E. coli* D12 HB101/pMND1006A, and *S. lividans*/pMND1006A. Moreover, of this preferred group, plasmids pMND1001, pMND1002, and pMND1003, and transformants *S. lividans*/pMND1001, *S. lividans*/pMND1002 and *S. lividans*/pMND1003 are most preferred.

The recombinant DNA cloning vectors and transformants of the present invention have broad utility and help fill the need for suitable cloning vehicles for use in *Streptomyces* and related organisms. Moreover, the ability of the present vectors to confer resistance to antibiotics that are toxic and non-transformed host cells, also provides a functional means for selecting transformants. This is important because of the practical necessity for determining and selecting the particular cells that have acquired vector DNA. Additional DNA segments, that lack functional tests for their presence, can also be inserted in the present vectors and then transformants containing the non-selectable DNA can be isolated by appropriate colorimetric or antibiotic selection. Such non-selectable DNA segments can be inserted at any site, execpt within regions necessary for plasmid function, maintainance, and replication, and include, but are not limited to, genes that specify antibiotic modification enzymes, antibiotic resistance, antibiotic biosynthesis, and regulatory genes of all types.

More particularly, a non-selectable DNA segment that comprises a gene can be inserted in a plasmid such as for example, illustrative plasmid pMND1005A, at the internal ClaI restriction site to inactive the thiostrepton resistance gene and thus allow for the easy identification of transformants containing the recombinant plasmid. This is done by first selecting for a mel$^{30}$ phenotype and then identifying those mel+ transformants that are not resistant to thiostrepton. In a similar manner, insertion of a DNA segment of interest at, for example, the single BglII restriction site of the ~1.5 kb BclI tyrosinase gene-containing fragment inactivates the tyrosinase gene. Thus, transformants carrying this recombinant plasmid also are identified easily by first selecting for thiostrepton resistance and then identifying those thiostrepton resistant transformants that do not exhibit a mel+ phenotype. Therefore, the ability to select for either antibiotic resistance or colorimetric phenotypes in *Streptomyces* and related cells allows for the efficient isolation of the extremely rare cells, out of billions of cells, that contain the particular nonselectable DNA of interest.

The functional test for antibiotic resistance or assay for colorimetric activity, as described herein above, is also used to locate DNA segments that act as control or biosynthetic elements and direct expression of antibiotic resistance genes. Such segments, including but not limited to, promoters, attenuators, repressors, inducers, ribosomal binding sites, and the like, are used to control the expression of other genes in cells of *Streptomyces* and related organisms.

The antibiotic resistance-conferring and colorimetric gene-containing vectors of the present invention are also useful for insuring that linked DNA segments are stably maintained in host cells over many generations. These genes or DNA fragments, covalently linked to thiostrepton or neomycin resistance-conferring fragment and propagated either in *Streptomyces* or in the cells of related organisms, are maintained by exposing the transformants to levels of thiostrepton or neomycin that are toxic to non-transformed cells. Therefore, transformants that lose the vector, and consequently and covalently linked DNA, cannot grow and are eliminated from the culture. In the case of the tyrosinase gene-containing fragments, transformants containing the linked DNA segment will produce a pigment providing a convenient means of detection and transformants that lose the vector will not exhibit this phenotype. Thus, the vectors of the present invention can stabilize and maintain any DNA sequence of interest.

The cloning vectors and transformants of the present invention provide for the cloning of genes to improve yields of various products that are currently produced in *Streptomyces* and related cells. Examples of such products include, but are not limited to, streptomycin, tylosin, cephalosproins, actaplanin, avoparcin, narasin, monensin, apramycin, tobramycin, erythromycin, tetracycline, chloramphenicol, vancomycin, teichomycin, and the like. The present invention also provides selectable vectors that are useful for cloning, characterizing, and reconstructing DNA sequences that code for commercially important proteins such as, for example, human insulin, human proinsulin, glucagon, intereferon, human growth hormone, inteleukin I, interleukin II, and the like; for enzymatic functions in metabolic pathways leading to commercially important processes and compounds; or for control elements that improve gene expression. These desired DNA sequences include, but are not limited to, DNA that codes for enzymes that catalyze synthesis of derivatized antibiotics such as, for example, streptomycin, cephalosporins, tylosin, actaplanin, avoparcin, narasin, monensin, apramycin, tobramycin, tetracycline, chloramphenicol, erythromycin, teichomycin, and vancomycin derivatives, or for enzymes that mediate and increase bioproduction of antibiotics or other products. The capability for inserting and stabilizing such DNA segments thus allows for increasing the yield and availability of antibiotics that are produced by *Streptomyces* and related organisms.

*Steptomyces lividans*, as a source of plasmid pMND1000 (NRRL 15808), can be cultured in a number of ways using any of several different media. Carbohydrate sources which are preferred in a culture medium include, for example, molasses, glucose, dextrin, and glycerol, and nitrogen sources include, for example, soy flour, amino acid mixtures, and peptones. Nutrient inorganic salts are also incorporated and include the customary salts capable of yielding sodium, potassium, ammonia, calcium, phosphate, chloride, sulfate, and like ions. As is necessary for the growth and development of other microorganisms, essential trace elements are also added. Such trace elements are commonly supplied as impurities incidental to the addition of other constituents of the medium.

*Streptomyces lividans* is grown under aerobic culture conditions over a relatively wide pH range of about 5 to 9 at temperatures ranging from about 15° to 40° C. For the production of plasmid pMND1000 in the greatest quantity, however, it is desirable to start with a culture medium at a pH of about 6.5 and maintain a culture temperature of about 30° C. Culturing the *Streptomyces* cells under the aforementioned conditions results in a reservoir of cells from which plasmid pMND1000 is isolated by techniques well known in the art.

BRIEF DESCRIPTION OF THE FIGURES

FIG. 3 is a restriction site and functional map of plasmids pMND1001 and pMND1001A.

FIG. 5 is a restriction site and functional map of plasmids pMND1004A and pMND1004B.

FIG. 6 is a restriction site and functional map of plasmids pMND1005A and pMND1005B.

FIG. 7 is a restriction site and functional map of plasmids pMND1006A and pMND1006B.

Figure 1:
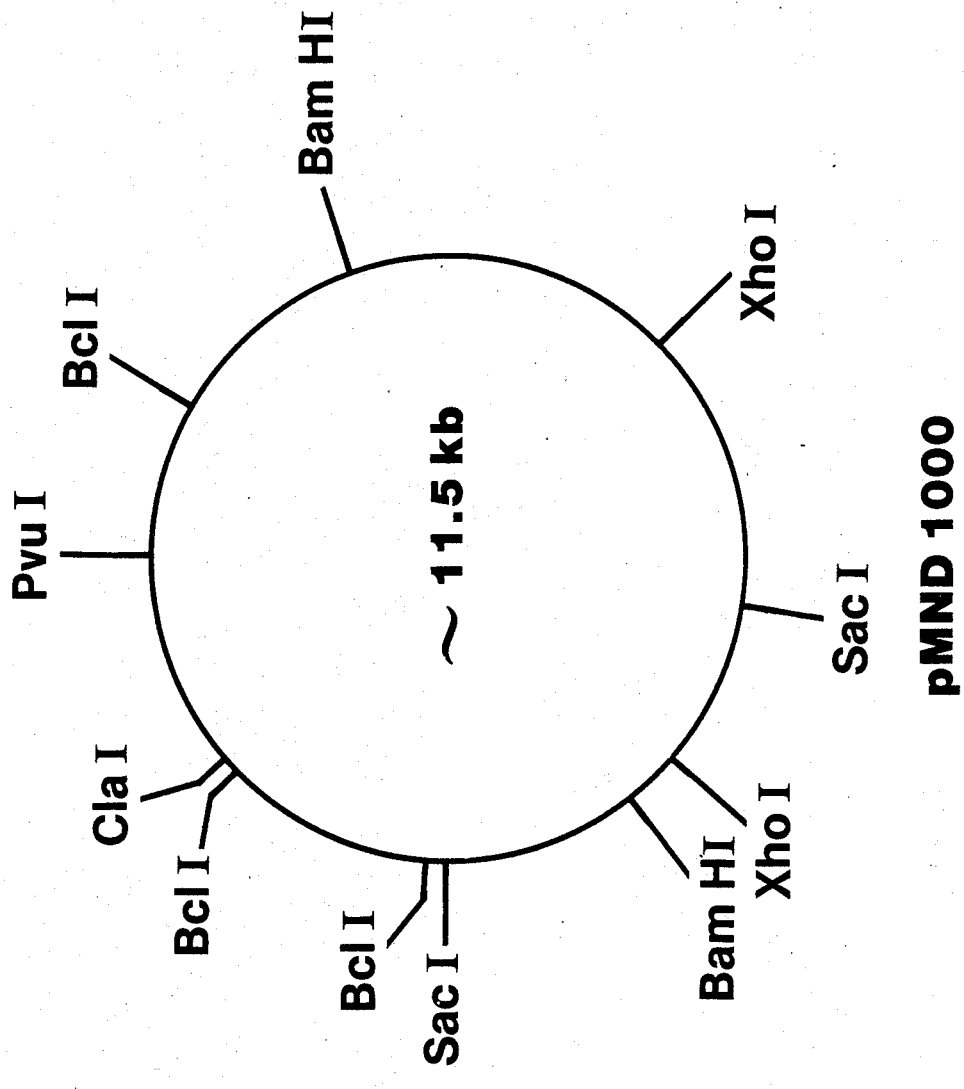
FIG. 1 shows the restriction site map of plasmid pMND1000.
Figure 2:
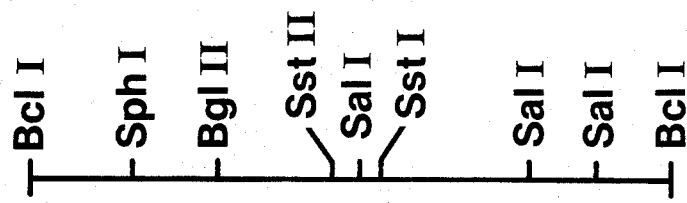
FIG. 2 is a linear restriction map of the ~1.5 kb tyrosinase gene-containing fragment of plasmid pIJ702.

The following examples further illustrate and detail the invention disclosed herein. Both an explanation of and the actual procedures for constructing the invention are described where appropriate.

EXAMPLE 1

Isolation of Plasmid pMND1000

A. Culture of *Streptomyces lividans* (NRRL 15808)

A vegetative inoculum of *Streptomyces lividans* NRRL 15808 was conventionally prepared by growing the strain under submerged aerobic conditions in 50 ml. of sterilized vegetative medium with the following preferred composition.

| Ingredient | Amount |
| --- | --- |
| Glucose | 20 g./l. |
| Nutrisoy flour* | 15 g./l. |
| Corn steep liquor* | 10 g./l. |
| CaCO$_3$ | 2 g./l. |
| Water (tap) | 1.1 l. |

*Nutrisoy flour is obtained from Archer Daniels Midland Company, 4666 Faries Parkway, Decatur, Illinois 62526.
*Corn steep liquor is obtained from CPC International, Corn Products, P.O. Box 3000, Englewood, N.J. 07632.

The vegetative inoculum was incubated for 48 hours at a temperature of 30° C. and a pH of 6.5. After incubation about 1.0 ml of the inoculum was transferred to 50 ml. of sterilized cell production medium with the following preferred composition.

| Ingredient | Amount |
| --- | --- |
| Trypticose soy broth* | 30 g./l. |
| Glucose | 10 g./l. |
| Glycine | 1 g./l. |
| Deionized water | 1.1 l. |

*Trypticase soy broth is obtained from Baltimore Biological Laboratories, P.O. Box 243, Cockeysville, Maryland 21031.

The inoculated cell production medium was incubated for about 20 hours at 30° C. The pH was not adjusted. After incubation, the *Streptomyces lividans* cells were ready for harvest and subsequent isolation of plasmid DNA.

B. Plasmid Isolation

About 10 g. (wet wgt.) of *Streptomyces lividans* cells were harvested by centrifugation (10 minutes, 5° C., 10,000 rpm). The cells were homogenized using a tissue grider, washed in TES buffer (0.05M tris(hydroxymethyl)aminomethane [tris], 0.005M EDTA, and 0.05M NaCl pH 8.0), and then suspended in TES buffer containing 25% sucrose. After the addition of about 120 mg. of lysozyme in 20 ml. of TES-25% sucrose buffer, the suspension was incubated at 35°–37° C. for about 20 minutes and, upon addition of 40 ml. of 0.25M EDTA pH 8.0, the suspension was again incubated at 35° C. for 10 minutes. Following this, about 40 ml. of 5% SDS (sodium dodecyl sulfate) in TE buffer (0.01M tris, 0.001M EDTA pH 8.0) was added and then, after the resultant mixture was again incubated at 35°–37° C. for 20 minutes, about 50 ml. of 5M NaCl in deionized water was added. The mixture was stirred, placed in an ice bath for about 4 hours and then centrifuged (30 minutes, 4° C., 10,000 rpm). About 0.313 volumes of 42% polyethylene glycol in deionized water were added to the NaCl supernatant and the resulting mixture was cooled at 4° C. for about 18 hours. The DNA precipitate was collected by centrifugation (5 minutes, 4° C., 3000 rpm) and was then dissolved in TES buffer at pH 8.0. Centrifugation (40 hours, 15° C., 35,000 rpm) using cesium chloride and ethidium bromide gradients separated the DNA into two well defined bands with the lower band consituting the desired plasmid DNA. Following conventional procedures, the band was removed, washed twice with isoamyl alcohol, dialyzed over TE buffer at pH 8.0 and precipitated with ethanol. The desired ~11.5 kb plasmid was isolated conventionally from the DNA suspension by agarose gel electrohoresis in substantial accordance with the teaching of Wieslander, L., 1979, Analytical Biochemistry 98: 305. The thus isolated plasmid pMND1000 DNA was dissolved in 0.4 ml. of TE buffer at pH 8.0 and was then frozen at −20° C. for storage.

EXAMPLE 2

Construction of Plasmids pMND1001 and pMND1001A

A. BamHI Digestion of Plasmid pLR2 and Isolation of the ~1.6 kb Thiostrepton Resistance-Conferring Fragment About 25 μg. of plasmid pLR2 DNA, the construction of which is disclosed in U.S. Pat. No. 4,416,994 and incorporated herein by reference, 10 μl. reaction mix*, 5 μl. 1M dithiothreitol, 10 μl. BSA (Bovine Serum albumin, 1 mg./ml.), 45 μl. water, and 5 μl. (4 units/μl.) of BamHI restriction enzyme** are incubated at 37° C. for 1 hour. After adding an equal volume of 4M ammonium acetate and 2 volumes of 95% ethanol, the mixture is cooled at −20° C. for about 18 hours to precipitate the DNA. The DNA precipitate is collected by centrifugation and then suspended in about 50 μl. of TE buffer. The desired ~1.6 kb BamHI restriction fragment can be isolated conventionally from the DNA suspension by agarose gel electrophoresis in substantial accordance with the teaching of Wieslander, 1979. Following isolation, the fragment is resuspended in about 20 μl. of TE buffer for subsequent ligation.

*Reaction mix for BamHI reaction mix was prepared with the following compositions.

1.5M NaCl
60 mM Tris-HCl, pH 7.9
60 mM MgCl₂

**Restriction enzymes and instructions can be obtained from the following sources:

New England Bio Labs., Inc.
32 Tozer Road
Beverly, Mass. 01915

Boehringer-Mannheim Biochemicals
7941 Castleway Drive
P.O. Box 50816
Indianapolis, Ind. 46250

Bethesda Research Laboratories Inc.
8717 Grovement Circle
P.O. Box 577
Gaithersburg, Md. 20760

B. BamHI Digestion of Plasmid pMND1000

The desired digestion was carried out in substantial accordance with the teaching of Example 2A except that plasmid pMND1000, rather than plasmid pLR2, was used.

C. Ligation

A mixture of about 20 μg. of BamHI restricted plasmid pMND1000 DNA, 10 μg. of the ~1.6 kb BamHI restriction fragment of plasmid pLR2, 5 μl. BSA (1 mg./ml.), 10 μl. ligation mix*, 45 μl. water and 3.5 μl. T4 DNA ligase** were incubated at about 16° C. for about 18 hours. After adding 0.1 volume of 3M ammonium acetate and 2 volumes of cold ethanol, the mixture was cooled to −20° C. for about 18 hours to precipitate the DNA. The DNA precipitate was collected by centrifugation, washed with 70% ethanol, collected again and then suspended in 50 μl. of P medium (Hopwood and Wright, 1978, J. Molecular and General Genetics 162: 307) for subsequent transformation:

*Ligation mix was prepared with the following composition.

500 mM Tris-HCl, pH 7.8
200 mM Dithiothreitol
100 mM MgCl₂
10 mM ATP

**T4 DNA ligase can be obtained from the same sources as those identified for restriction enzymes.

Recombinant plasmids of two orientations, each with the desired phenotype, result depending upon the orientation of the inserted ~1.6 kb BamHi thiostrepton resistance-conferring fragment. Plasmid pMND1001 designates the resulting recombinant plasmid in which the subterminal PvuI restriction site adjacent to the BamHI restriction site of the resistance-conferring fragment is inserted closest to the flanking XhoI site of plasmid pMND1000. Plasmid pMND1001A designates the recombinant plasmid with the reverse orientation. A restriction site and functional map of each of plasmids pMND1001 and pMND1001A is presented in FIG. 3 of the accompanying drawings.

EXAMPLE 3

Construction of Plasmids pMND1002 and pMND1002A

The desired construction was carried out in substantial accordance with the teaching of Example 2 except that plasmid pMND1000 was digested with BclI restriction enzyme and reaction mix (12 mM NaCl, 12 mM Tris-HCl pH 7.4, 12 mM MgCl₂, and 0.5 mM Dithiothreitol) in place of BamHI restriction enzyme and reaction mix. In addition, the reaction was run at 50° C. for 2 hours. The ~9.1 kb BClI restriction fragment was isolated and purified away from the smaller BclI generated fragments.

The above procedure resulted in the replacement of the small BclI fragment of plasmid pMND1000 with the ~1.6 kb BamHI-restricted thiostrepton-resistance conferring gene of plasmid plasmid pLR2.

EXAMPLE 4

Construction of Plasmid pMND1003

A. XhoI Digestion of Plasmid pMND1002

Plasmid pMND1003 was constructed by deleting a XhoI fragment from plasmid pMND1002. The desired digestion was carried out in substantial accordance with the teaching of Example 2B except that plasmid pMND1002 was used in place of plasmid pMND1000. In addition, XhoI restriction enzyme and reaction mix (150 mM NaCl, 6 mM Tris-HCl pH 7.9, 6 mM MgCl₂, 6 mM 2-mercaptoethanol, and 100 μg/ml BSA) were used in place of BamHI restriction enzyme and reaction mix. The ~8.8 kb XhoI restriction fragment was isolated and purified away from the smaller XhoI generated fragment.

B. Self Ligation of XhoI-Digested DNA from Example 4A

Figure 4:
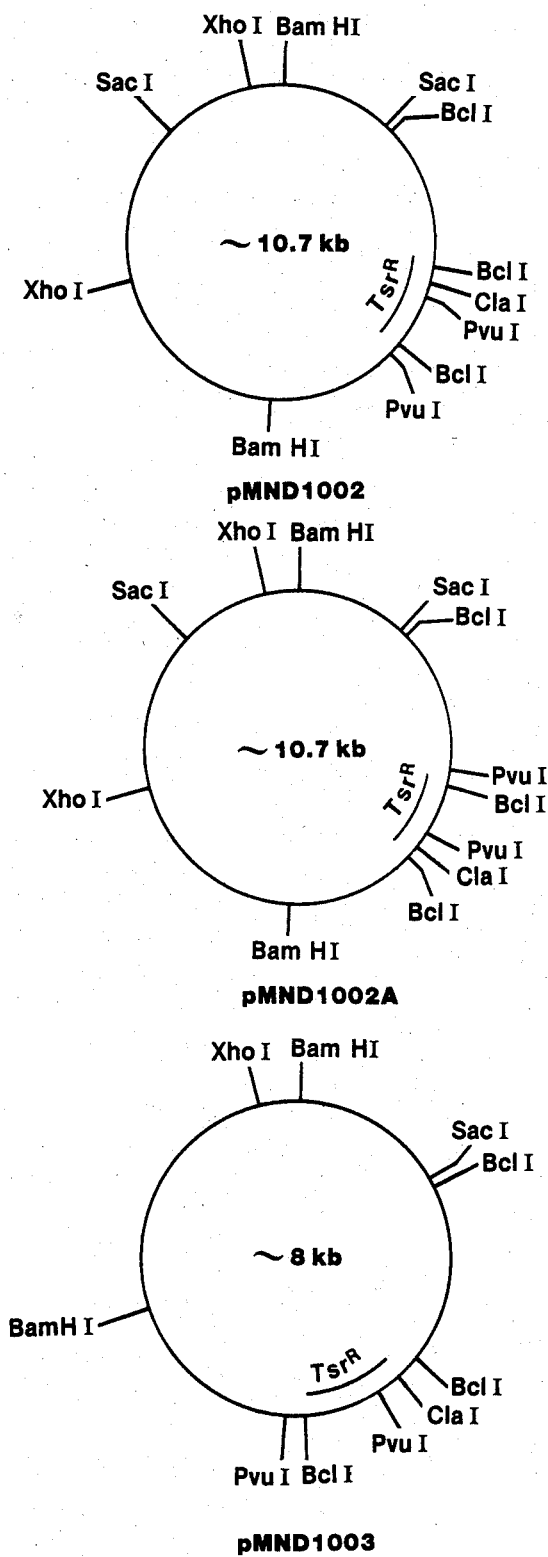
FIG. 4 is a restriction site and functional map of plasmids pMND1002, pMND1002A, pMND1003.

The desired ligation was carried out in substantial accordance with Example 2C except that the XhoI-digested DNA isolated in Example 4A is used in place of BamHI-treated pMND1000 and BamHI-treated pLR2. The suspended DNA constitutes the desired plasmid pMND1003. A restriction site and functional map of plasmid pMND1003 is presented in FIG. 4 of the accompanying drawings.

EXAMPLE 5

Construction of *Streptomyces lividans*/pMND1001 *S. lividans*/pMND1002 and *S. lividans*/pMND1003

Using about 2 μg. DNA from Examples 2, 3, and 4, respectively, and $1\times 10^8$ protoplasts of *Streptomyces lividans* (NRRL 15825), the desired constructions were individually made, selected, and recovered in substantial accordance with the teaching of International Publication (of International Patent Application No. PCT/6B 79/0095) No. WO69/01169, Example 2. The desired transformants were selected for thiostrepton resistance by plating on Bennett's Modified Medium* containing sufficient thiostrepton** to bring the final plate concentration to 50 μg./ml. The resulting *Streptomyces lividans*/pMND1001, *S. lividans*/pMND1002, and *S. lividans*/pMND1003 thiostrepton resistant colonies were isolated, cultured and then conventionally identified by restriction enzyme and agarose gel electrophoretic analysis of the constitutive plasmids (Wieslander, 1979). The transformant cultures were used for subsequent production and isolation of their respective plasmids.

*Bennett's medium (Agar), disclosed in Waksman, 1961, The Actionmycetes, Volume II, The Williams and Wilkins Company, Baltimore, Md., was modified by adding $CoCl_2.6H_2O$(0.01 g./L.) and by replacing glucose with dextrin.

**Antibiotic thiostrepton can be obtained from E. R. Squibb and Sons, Inc., Princeton, N.J. 08540.

EXAMPLE 6

Construction of Plasmids pMND1004A and pMND1004B

A. BamHI Digestion of Plasmid pLR1 and Isolation of the ~3.4 kb Neomycin Resistance-Conferring Fragment The desired digestion is carried out in substantial accordance with the teaching of Example 2A except that plasmid pLR1, the construction of which is disclosed in U.S. Pat. No. 4,416,994 and incorporated herein by reference, is used in place of plasmid pLR2.

B. BclI and XhoI Digestion of Plasmid pMND1000

About 10 μg. of plasmid pMND1000 is digested in substantial accordance with the teaching of Example 3 except that XhoI restriction enzyme and reaction mix are used in addition to BclI restriction enzyme and reaction mix. The ~3.4 BclI-XhoI restriction fragment was isolated and purified away from the other resulting fragments. The XhoI-generated end is filled in with Klenow Polymerase I as described in Maniatis et al., 1982, Molecular Cloning, Cold Spring Harbor Laboratory, Cold Spring Harbor, N.Y. This fragment now consists of a staggered BclI-end and a blunt end. This blunt end is next combined with BclI linkers (available from Collaborative Research, Inc., 128 Spring Street, Lexington, Mass. 02173) providing a BclI cleavage site for ligation to the ~3.4 kb BamHI restriction fragment of plasmid pLR1. The 10 μg. of DNA fragments obtained from pLR1 (from Example 6A) are treated with 10 units T4 DNA ligase in the presence of 200 picomoles of the 5'-phosphorylated synthetic oligonucleotide and in 20 μl. T4 DNA ligase buffer (20 mM Tris pH 7.6, 0.5 mM ATP, 10 mM $MgCl_2$, 5 mM Dithiothreitol) at 20°–22° C. overnight. The ligation is then heated 10 minutes at 70° C. to halt ligation. The linkers are cleaved by BclI digestion and the fragments, now with BclI ends, are separated using 1 percent AGE (agarose gel electrophoresis). The ~3.4 kb fragment is isolated from the gel in substantial accordance with the teaching of Wieslander, 1979.

Recombinant plasmids of two orientations, each with the desired phenotype, result depending upon the orientation of the inserted ~3.4 bk BamHI neomycin resistance-conferring fragment. Thus, the final DNA suspension contains plasmids pMND1004A and pMND1004B. Plasmid pMND1004A designates the recombinant plasmid in which the subterminal PstI restriction site of the resistance-conferring fragment is inserted closest to the flanking BamHI site of the parental plasmid pMND1000. Plasmid pMND1004B designates the recombinant plasmid with the reverse orientation. A restriction site and functional map of each of plasmids pMND1004A and pMND1004B is presented in FIG. 5 of the accompanying drawings.

EXAMPLE 7

Construction of Plasmid pMND1005A and pMND1005B

A. BamHI Digestion of Plasmid pMND1003

The desired digestion is carried out in substantial accordance with the teaching of Example 2A except that plasmid pMND1003, rather than plasmid pLR2, is used.

B. Isolation of the ~1.5 kb BclI Tyrosinase Gene Fragment of Plasmid pIJ702

About 20 μl. (20 μg.) of plasmid pIJ702 DNA, (which can be conventionally isolated from *Streptomyces lividans*/pIJ702 (ATCC 39155) in substantial accordance with the teaching of Example 1), 10 μl. BSA (1 mg./ml.), 55 μl. water, 5 μl. of BclI restriction enzyme, and 10 μl. reaction mix are incubated at 50° C. for 4 hours. The reaction is terminated by precipitation with ethanol. The DNA is pelleted, dried and resuspended in 50 μl. of 1/10 TE.

C. Ligation

The desired ligation is conveniently done by adding the BamHI digested fragment of Example 7A to the ~1.5 kb BclI digested tyrosinase gene fragment isolated above by use of T4 DNA ligase. Ligation is performed in substantial accordance with the teaching of Example 2C. Recombinant plasmids of two orientations are produced since the tyrosinase gene fragment, as previously discussed with respect to the antibiotic resistantce-containing fragments, can be inserted in either orientation in the available BamHI site. Plasmid pMND1005A designates the resulting recombinant plasmid in which the subterminal BglII restriction site of the tyrosinase gene fragment is inserted closest to the unique XhoI site of plasmid pMND1003. Plasmid pMND1005B designates the recombinant plasmid with the reverse orientation. A restriction site and functional map of plasmids pMND1005A and pMND1005B is presented in FIG. 6 of the accompanying drawings.

EXAMPLE 8

Construction of Plasmids pMND1006A and pMND1006B

A. BamHI Digestion of Plasmid pBR322

The desired digestion is carried out in substantial accordance with Example 2A except that plasmid pBR322 is used in place of plasmid pLR2.

B. Ligation

The desired ligation is carried out by reacting about 20 μg. of BamHI restricted plasmid pMND1003 DNA (prepared in Example 7A) and about 19 μg. of the BamHI restricted pBR322 DNA in substantial accordance with the teaching of Example 2C.

Recombinant plasmids of two orientations, each with the desired phenotype, result because the BamHI restricted plasmid pBR322 can be oriented in either direction. A restriction site and functional map of plasmids pMND1006A and pMND1006B is presented in FIG. 7 of the accompanying drawings.

EXAMPLE 9

Construction of *Streptomyces lividans*/pMND1004A and *S. lividans*/pMND1004B Using about 2 μg. DNA from Example 6 and $1 \times 10^8$ protoplasts of *Streptomyces lividans*, (NRRL 15825), the desired constructions are made in substantial accordance with the teaching of International Publication (of International Patent Application No. PCT/GB 79/00095) No. WO79/01169, Example 2. The desired transformants are selected for neomycin resistance by plating on Bennett's Modified Medium containing about 1 μg./ml. of antibiotic neomycin*. The resulting *Streptomyces lividans*/pMND1004 and *S. lividans*/pMND1004B neomycin resistant colonies are isolated, cultured and then conventionally identified by restriction enzyme and agarose gel electrophoretic analysis of the constitutive plasmids (Wieslander, 1979). The transformant cultures are used for subsequent production and isolation of their respective plasmids.

*Antibiotic neomycin can be obtained from Sigma, St. Louis, Mo.

EXAMPLE 10

Construction of *Streptomyces lividans*/pMND1005A and *S. lividans*/pMND1006A Using about 2 μg. DNA from Examples 7 and 8, respectively, and $1 \times 10^8$ protoplasts of *Streptomyces lividans* (NRRL 15825), the desired constructions are individually made, selected, and recovered in substantial accordance with the teaching of International Publication (of International Patent Application No. PCT/6B 79/0095) No. WO79/01169, Example 2. The desired transformants are selected for thiostrepton resistance by plating on Bennett's Modified Medium* containing sufficient thiostrepton** to bring the final plate concentration to 50 μg./ml. In addition, *S. lividans*/pMND1005A transformants are selected for the resulting mel+ phenotype. The resulting *Streptomyces lividans*/pMND1005A and *S. lividans*/pMND1006A thiostrepton resistant colonies are isolated, cultured and then conventionally identified by restriction enzyme and agarose gel electrophoretic analysis of the constitutive plasmids (Wieslander, 1979). The transformant cultures can then be used for subsequent production and isolation of their respective plasmids.

*Bennett's medium (Agar), disclosed in Waksman, 1961, The Acrtionmycetes, Volume II, The Williams and Wilkins Company, Baltimore, Md., was modified by adding $CoCl_2.6H_2O$(0.01 g./L.) and by replacing glucose with dextrin.
**Antibiotic thisotrepton can be obtained from E. R. Squibb and Sons, Inc. Princeton, N.J. 08540.

EXAMPLE 11

Construction of *E. coli* K12 HB101/pMND1006A

About 1 ml. of frozen competent *E. coli* K12 HB101 cells (NRRL B-15626) is brought to 0° C.

Plasmid pMND1006A in TE buffer (prepared in Example 8) is ethanol precipitated, suspended in 50 μl. of 30 mM calcium chloride solution, and gently mixed in a test tube with about 100 μl. of competent *E. coli* K12 HB101 cells. The resulting mixture is incubated on ice for about 45 minutes and then at 42° C. for about 1 minute. Next, about 3 ml. of L-broth (Bertani, 1951, J. Bacteriology 62: 293) containing 50 μg./ml. of ampicillin is added. The mixture is incubated with shaking at 37° C. for 1 hour and then plated on L-agar (Miller, 1972, Experiments in Molecular Genetics, Cold Spring Harbor Laboratory, Cold Spring Harbor, N.Y.) containing ampicillin. Surviving colonies are first selected, and tested for the expected phenotype ($Ap^R$, $Tet^S$), and then conventionally identified as the desired *E. coli* K12 HB101/pMND1006A transformants by restriction enzyme and gel electrophoretic analysis of the constitutive plasmids.

Representative transformants constructed in accordance with the foregoing teaching include the following listed in Table 1 below.

TABLE 1

Representative Transformants

1. Streptomyces R/R[1] wherein R is *ambofaciens, aureofaciens, griseofuscus, fradiae\*, lividans, cinnamonensis, coelicolor* or *toyocaensis* and wherein R[1] independently is a plasmid from the group consisting of pMND1001, pMND1001A, pMND1002, pMND1002A, pMND1003, pMND1004A, pMND1004B, pMND1005A, pMND1005B, pMND1006A and pMND1006B.

*The following procedure is used for transforming *S. fradiae*. Use low OD cells (less than 4 O.D. units) grown at 29° C. in the presence of 0.4% glycine in TSB medium. Protoplasts are formed in the presence of 1 mg./ml. lysozyme in P medium on ice followed by two washes with P medium. Chill for 1–3 hours and then warm to ambient temperature. Mix 0.8 μg. calf thymus DNA and 1.5 μg. protamine sulfate for one minute, then add: purified plasmid DNA (less than 100 ng.) suspended in 10 μl. of P medium, 200 μl. of diluted protoplasts (⅓x), 0.9 ml. of 55% PEG 1000 and mix for one minute. Using soft agar overlays, plate protoplasts and incubate at 29° C. for 16–24 hours then overlay with the appropriate antibiotic. Reincubate at 29° C. and score the plates in 7–10 days.

We claim:

1. A recombinant DNA cloning vector comprising:
   (a) a functional origin of replication-containing restriction fragment of plasmid pMND1000, and
   (b) one or more DNA segments that convey resistance to at least one antibiotic or that convey colorimetric sensitivity when transformed into a sensitive restrictionless host cell.

2. The cloning vector of claim 1 wherein the restriction fragment of pMND1000 is the ~3.4 lb XhoI-BclI restriction fragment.

3. The ~3.4 kb XhoI-BclI restriction fragment of claim 2.

4. The recombinant DNA cloning vector of claim 1 selected from the group consisting of plasmids pMND1001, pMND1001A, pMND1002, pMND1002A, pMND1003, pMND1004A, pMND1004B, pMND1005A and pMND1005B.

5. The cloning vector of claim 4 which is plasmid pMND1001.

6. The cloning vector of claim 4 which is plasmid pMND1002.

7. The cloning vector of claim 4 which is plasmid pMND1003.

8. A transformed restrictionless host cell comprising a recombinant DNA cloning vector of claim 1.

9. The transformed host cell of claim 8 which is restrictionless Streptomyces.

10. The transformed host cell of claim 8 in which the recombinant DNA cloning vector is selected from the group consisting of plasmids pMND1001, pMND1001A, pMND1002, pMND1002A, pMND1003, pMND1004A, pMND1004B, pMND1005A and pMND1005B.

11. The transformed host cell of claim 10 which is restrictionless Streptomyces.

12. The transformed Streptomyces of claim 11 which is *Streptomyces ambofaciens*.

13. The transformed Streptomyces of claim 11 which is *Streptomyces griseofuscus*.

14. The transformed Streptomyces of claim 11 which is *Streptomyces coelicolor*.

15. The transformed Streptomyces of claim 11 which is *Streptomyces lividans*.

16. The transformed host cell of claim 11 which is *Streptomyces lividans*/pMND1001.

17. The transformed host cell of claim 11 which is *Streptomyces lividans*/pMND1002.

18. The transformed host cell of claim 11 which is *Streptomyces lividans*/pMND1003.

19. A recombinant DNA cloning vector of claim 1 comprising in addition:
(c) a functional original of replication-containing fragment of an *E. coli* plasmid.

20. The recombinant DNA cloning vector of claim 19 wherein the functional origin of replication-containing fragment of the *E. coli* plasmid is selected from the group consisting of origin replication-containing fragments of plasmids pBR322, pBR325, and pBR328.

21. The recombinant DNA cloning vector of claim 19 which is selected from the group consisting of plasmids pMND1006A and pMND1006B.

22. A transformed restrictionless host cell selected from the group consisting of Streptomyces, Nocardia, and *E. coli*, which comprises a recombinant DNA cloning vector of claim 21.

23. A transformed restrictionless host cell which is Streptomyces R/R' wherein R is *ambofaciens, aureofaciens, cinnamonensis, coelicolor, fradiae, griseofuscus, lividans, or toyocaensis* and wherein R' independently is selected from the group consisting of plasmids pMND1001, pMND1001A, pMND1002, pMND1002A, pMND1003, pMND1004A, pMND1004B, pMND1005A and pMND1005B.

24. Plasmid pMND1000.

* * * * *

UNITED STATES PATENT AND TRADEMARK OFFICE
CERTIFICATE OF CORRECTION

PATENT NO. : 4,698,307

DATED : October 6, 1987

INVENTOR(S) : James A. Mabe and Walter M. Nakatsukasa

It is certified that error appears in the above-identified patent and that said Letters Patent is hereby corrected as shown below:

Column 3, line 50, "frgment" should read --fragment--.

Column 5, line 10, "MND1004A" should read --pMND1004A--.

Column 7, line 3, "usefull" should read --useful--.

Column 7, line 48, "D12" should read --K12--.

Column 8, line 1, "execpt" should read --except--.

Column 8, line 12, "mel$^{30}$" should read --mel$^+$--.

Column 8, line 68, "intereferon" should read --interferon--.

Column 9, line 1 should read --human growth hormone, avian growth hormone, bovine growth hormone, porcine growth hormone, interleukin I, interleukin II--, Column 9, line 17, "Steptomyces" should read --Streptomyces--.

Column 10, line 63, "consituting" should read --constituting--.

Column 10, line 68, "electrohoresis" should read --electrophoresis--.

UNITED STATES PATENT AND TRADEMARK OFFICE
CERTIFICATE OF CORRECTION

PATENT NO. : 4,698,307

DATED : October 6, 1987

INVENTOR(S) : James A. Mabe and Walter M. Nakatsukasa

It is certified that error appears in the above-identified patent and that said Letters Patent is hereby corrected as shown below:

Column 12, line 12, "Reconbinant" should read --Recombinant--.

Column 12, line 14, "BamHi" should read --BamHI--.

Column 13, line 14, "WO69/01169" should read --WO79/01169--.

Column 15, penultimate line, "Acrtion-" should read --Action--.

Column 16, line 62, "lb" should read --kb--.

Signed and Sealed this

Twenty-ninth Day of October, 1991

Attest:

HARRY F. MANBECK, JR.

*Attesting Officer*   *Commissioner of Patents and Trademarks*